United States Patent
Brown

(10) Patent No.: US 8,563,758 B2
(45) Date of Patent: Oct. 22, 2013

(54) METHOD OF SYNTHESIS OF SUBSTITUTED HEXITOLS SUCH AS DIANHYDROGALACTITOL

(75) Inventor: Dennis M. Brown, Menlo Park, CA (US)

(73) Assignee: Del Mar Pharmaceuticals, Vancouver (CA)

( * ) Notice: Subject to any disclaimer, the term of this patent is extended or adjusted under 35 U.S.C. 154(b) by 0 days.

(21) Appl. No.: 13/817,046

(22) PCT Filed: Aug. 17, 2011

(86) PCT No.: PCT/US2011/048032
§ 371 (c)(1), (2), (4) Date: Apr. 29, 2013

(87) PCT Pub. No.: WO2012/024368
PCT Pub. Date: Feb. 23, 2012

(65) Prior Publication Data
US 2013/0211111 A1    Aug. 15, 2013

Related U.S. Application Data

(60) Provisional application No. 61/401,710, filed on Aug. 18, 2010.

(51) Int. Cl.
C07D 301/26 (2006.01)
C07D 303/14 (2006.01)

(52) U.S. Cl.
USPC .......................................... 549/521; 549/555

(58) Field of Classification Search
USPC ................................................... 549/521, 555
See application file for complete search history.

(56) References Cited

U.S. PATENT DOCUMENTS 7,157,079 B2 *    1/2007   Nielsen et al. ............... 424/93.2

* cited by examiner

Primary Examiner — Bernard Dentz
(74) Attorney, Agent, or Firm — Ditthavong Mori & Steiner, P.C.

(57) ABSTRACT

The present invention provides an efficient method of synthesizing and purifying dianhydrohexitols such as dianhydrogalactitol. In general, as applied to dianhydrogalactitol, the method comprises: (1) reacting dulcitol with a concentrated solution of hydrobromic acid at a temperature of about 80° C. to produce dibromogalactitol; (2) reacting the dibromogalactitol with potassium carbonate in t-butanol to produce dianhydrogalactitol; and (3) purifying the dianhydrogalactitol using a slurry of ethyl ether to produce purified dianhydrogalactitol.

20 Claims, No Drawings

METHOD OF SYNTHESIS OF SUBSTITUTED HEXITOLS SUCH AS DIANHYDROGALACTITOL

CROSS-REFERENCES

This application claims priority from U.S. Provisional Application Ser. No. 61/401,710, by Dennis M. Brown, Ph.D., filed Aug. 18, 2010, and entitled "Method of Synthesis of Substituted Hexitols Such as Dianhydrogalactitol," which is incorporated herein in its entirety by this reference.

TECHNICAL FIELD OF THE INVENTION

The present invention is directed to improved methods for the synthesis of substituted hexitols, especially dianhydrogalactitol.

BACKGROUND OF THE INVENTION

A number of substituted hexitols, such as dianhydrogalactitol, have pharmacological activities. In particular, dianhydrogalactitol has been suggested for use in chemotherapy, such as in U.S. Pat. No. 7,157,079 to Nielsen et al., incorporated herein by this reference.

However, current methods of synthesis of such substituted hexitols, such as dianhydrogalactitol, are inefficient, and improved methods of synthesis of these substituted hexitols are required in order to provide larger quantities of these compounds for clinical use.

SUMMARY OF THE INVENTION

An improved method of synthesis of dianhydrohexitols such as dianhydrogalactitol comprises conversion of the hexitol to a dibromohexitol by reaction with concentrated hydrobromic acid, followed by conversion of the dibromohexitol to the dianhydrohexitol by reaction with potassium carbonate.

In general, as applied to the synthesis of dianhydrogalactitol, the method comprises the steps of:

(1) reacting dulcitol with a concentrated solution of hydrobromic acid at a temperature of about 80° C. to produce dibromogalactitol;

(2) reacting the dibromogalactitol with potassium carbonate in t-butanol to produce dianhydrogalactitol; and (3) purifying the dianhydrogalactitol using a slurry of ethyl ether to produce purified dianhydrogalactitol.

In this method, typically, the concentrated solution of hydrobromic acid is about 70% hydrobromic acid and is produced by reacting phosphorus with bromine in hydrobromic acid at elevated temperature. Typically, the dibromogalactitol is dissolved in t-butanol in a proportion of about 1 g of dibromogalactitol to 10 mL of t-butanol.

In this method, typically, the dulcitol is purified from the plant *Maytenus confertiflora* by the steps of:

(a) soaking the plant *Maytenus confertiflora* in a soaking solution of from about 50% to about 80% of ethanol for about 24 hours;

(b) collecting the soaking solution from step (a);

(c) repeating the soaking step of step (a) with a fresh soaking solution of from about 50% to about 80% of ethanol for about 24 hours;

(d) collecting the soaking solution from step (c) and combining it with the soaking solution collected in step (b);

(e) removing the solvent from the combined soaking solutions of step (d) by heating under reduced pressure to produce a concentrated solution;

(f) allowing the concentrated solution of step (e) to settle overnight and collecting the clear supernatant;

(g) extracting the clear supernatant from step (f) with chloroform and then removing the chloroform under heat and reduced pressure;

(h) dissolving the residue from step (g) in hot methanol and then cooling to allow crystallization; and (i) collecting the collected crystals of dulcitol, filtering, and drying the crystals under reduced pressure.

Although this method is described for the synthesis and purification of dianhydrogalactitol, it is not limited to dianhydrogalactitol, and can be applied to other hexitols bearing two epoxide groups such as substituted dianhydrogalactitols.

More generally, a method according to the present invention for synthesizing and purifying a dianhydrohexitol comprises the steps of:

(1) reacting a hexitol bearing two epoxide groups with a concentrated solution of hydrobromic acid at a temperature of about 80° C. to produce a dibromohexitol;

(2) reacting the dibromohexitol with a carbonate salt of an alkali metal in a tertiary alcohol to produce a dianhydrohexitol; and (3) purifying the dianhydrohexitol using a slurry of an ether to produce the purified dianhydrohexitol.

Typically, the dianhydrohexitol is selected from the group consisting of dianhydrogalactitol and a substituted dianhydrogalactitol. Preferably, the dianhydrohexitol is dianhydrogalactitol.

Typically, the concentrated solution of hydrobromic acid is about 70% hydrobromic acid and is produced by reacting phosphorus with bromine in hydrobromic acid at elevated temperature.

Typically, the tertiary alcohol is selected from the group consisting of t-butanol, 2-methyl-2-butanol, and 3-ethylpentanol. Preferably, the tertiary alcohol is t-butanol.

Typically, the dibromohexitol is dissolved in the tertiary alcohol in a proportion of about 1 g of dibromohexitol to 10 mL of tertiary alcohol.

Typically, the dibromohexitol is purified by recrystallization prior to its conversion to dianhydrohexitol.

Typically, the carbonate salt of the alkali metal is a carbonate salt of an alkali metal selected from the group consisting of sodium carbonate and potassium carbonate. Preferably, the carbonate salt of the alkali metal is potassium carbonate.

Typically, the ether is an aliphatic ether with lower alkyl groups. Preferably, the ether is selected from the group consisting of dimethyl ether, methyl ethyl ether, diethyl ether, dipropyl ether, methyl propyl ether, and ethyl propyl ether. More preferably, the ether is diethyl ether.

DETAILED DESCRIPTION OF THE INVENTION

Dianhydrogalactitol (DAG or dianhydrodulcitol) can be synthesized from dulcitol which can be produced from natural sources (such as *Maytenus confertiflora*) or commercial sources.

The structure of DAG is given below as Formula (I).

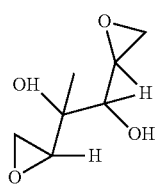

One method for the preparation of dulcitol from *Maytenus confertiflora* is as follows: (1) The *Maytenus confertiflora* plant is soaked in diluted ethanol (50-80%) for about 24 hours, and the soaking solution is collected. (2) The soaking step is repeated, and all soaking solutions are combined. (3) The solvent is removed by heating under reduced pressure. (4) The concentrated solution is allowed to settle overnight and the clear supernatant is collected. (5) Chloroform is used to extract the supernatant. The chloroform is then removed under heat and reduced pressure. (6) The residue is then dissolved in hot methanol and cooled to allow crystallization. (7) The collected crystals of dulcitol are filtered and dried under reduced pressure. The purified material is dulcitol, contained in the original *Maytenus confertiflora* plant at a concentration of about 0.1% (¹⁄₁₀₀₀).

DAG can be prepared by two general synthetic routes as described below:

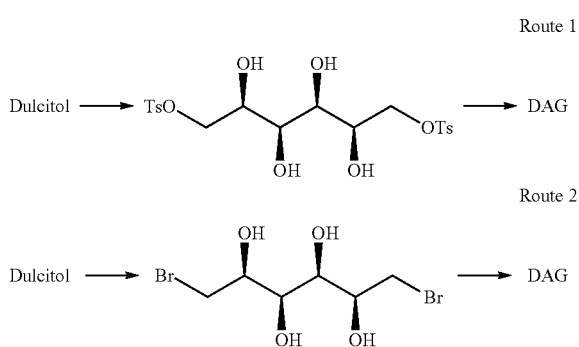

In Route 1, "Ts" represents the tosyl group, or p-toluenesulfonyl group.

However, the intermediate of Route 1, 1,6-ditosyldulcitol, was prepared with low yield (~36%), and the synthesis of 1,6-ditosyldulcitol was poorly reproducible. Therefore, the second route process was developed, involving two major steps: (1) preparation of dibromodulcitol from dulcitol; and (2) preparation of dianhydrodulcitol from dibromodulcitol.

Dibromodulcitol is prepared from dulcitol as follows: (1) With an aqueous HBr solution of approximately 45% HBr concentration, increase the HBr concentration to about 70% by reacting phosphorus with bromine in concentrated HBr in an autoclave. Cool the solution to 0° C. The reaction is: $2P + 3Br_2 \rightarrow 2PBr_3 + H_2O \rightarrow HBr\uparrow + H_3PO_4$. (2) Add the dulcitol to the concentrated HBr solution and reflux at 80° C. to complete the reaction. (3) Cool the solution and pour the mixture onto ice water. Dibromodulcitol is purified through recrystallization.

The results for the preparation of dibromodulcitol (DBD) are shown in Table 1, below.

TABLE 1

| Dulcitol | 18 g | 18 g | 18 g | 18 g |
|---|---|---|---|---|
| 45% aq. HBr | 36 mL | 36 mL | 36 mL | 36 mL |
| PBr₃ | 40 g | 40 g | 40 g | 40 g |
| Time | 7 h | 7 h | 7 h | 7 h |
| Temp/° C. | 70 | 70 | 70 | 70 |
| Crude Product | 25.2 g | 25.5 g | 24 g | 24.7 g |
| Yield | 84% | 85% | 80% | 82% |

For the preparation of DAG from DBD, DBD was poorly dissolved in methanol and ethanol at 40° C. (different from what was described in U.S. Pat. No. 3,993,781 to Horvath nee Lengyel et al., incorporated herein by this reference). At refluxing, DBD was dissolved but TLC showed that new impurities formed that were difficult to remove from DBD.

The DBD was reacted with potassium carbonate to convert the DBD to dianhydrogalactitol.

The results are shown in Table 2, below.

TABLE 2

| DBD | 0.5 g | 5 g | 4.3 g |
|---|---|---|---|
| K₂CO₃ | 1 g | 8 g | 4 g |
| t-BuOH | 5 mL | 50 mL | 40 mL |
| DAG | 0.17 g | 1 g | 0.82 g |
| Yield | 72% | 42% | 40% |

In the scale-up development, it was found the crude yield dropped significantly. It is unclear if DAG could be azeotropic with BuOH. It was confirmed that t-BuOH is essential to the reaction. Using MeOH as solvent would result in many impurities as shown spots on TLC. However, an improved purification method was developed by using a slurry with ethyl ether, which could provide DAG with good purity. This was developed after a number of failed attempts at recrystallization of DAG.

Accordingly, one aspect of the present invention is a method for synthesizing and purifying dianhydrogalactitol (DAG) comprising the steps of:

(1) reacting dulcitol with a concentrated solution of hydrobromic acid at a temperature of about 80° C. to produce dibromogalactitol;

(2) reacting the dibromogalactitol with potassium carbonate in t-butanol to produce dianhydrogalactitol; and (3) purifying the dianhydrogalactitol using a slurry of ethyl ether to produce purified dianhydrogalactitol.

In this method, typically, the concentrated solution of hydrobromic acid is about 70% hydrobromic acid and is produced by reacting phosphorus with bromine in hydrobromic acid at elevated temperature. Typically, the dibromogalactitol is dissolved in t-butanol in a proportion of about 1 g of dibromogalactitol to 10 mL of t-butanol. Typically, the dibromogalactitol is purified by recrystallization prior to its conversion to dianhydrogalactitol.

In this method, typically, the dulcitol is purified from the plant *Maytenus confertiflora* by the steps of:

(a) soaking the plant *Maytenus confertiflora* in a soaking solution of from about 50% to about 80% of ethanol for about 24 hours;

(b) collecting the soaking solution from step (a);

(c) repeating the soaking step of step (a) with a fresh soaking solution of from about 50% to about 80% of ethanol for about 24 hours;

(d) collecting the soaking solution from step (c) and combining it with the soaking solution collected in step (b);

(e) removing the solvent from the combined soaking solutions of step (iv) by heating under reduced pressure to produce a concentrated solution;

(f) allowing the concentrated solution of step (e) to settle overnight and collecting the clear supernatant;

(g) extracting the clear supernatant from step (f) with chloroform and then removing the chloroform under heat and reduced pressure;

(h) dissolving the residue from step (g) in hot methanol and then cooling to allow crystallization; and (i) collecting the collected crystals of dulcitol, filtering, and drying the crystals under reduced pressure.

Another embodiment of the invention is a method for synthesizing and purifying a dianhydrohexitol comprising the steps of:

(1) reacting a hexitol bearing two epoxide groups with a concentrated solution of hydrobromic acid at a temperature of about 80° C. to produce a dibromohexitol;

(2) reacting the dibromohexitol with a carbonate salt of an alkali metal in a tertiary alcohol to produce a dianhydrohexitol; and (3) purifying the dianhydrohexitol using a slurry of an ether to produce the purified dianhydrohexitol.

In this method, the dianhydrohexitol can be, for example, dianhydrogalactitol or another dianhydrohexitol that has two epoxide groups, such as a substituted dianhydrogalactitol, as described above. However, typically the dianhydrohexitol is dianhydrogalactitol.

In this method, the carbonate salt of the alkali metal is typically a carbonate salt of an alkali metal selected from the group consisting of sodium carbonate and potassium carbonate. Preferably, the carbonate salt of the alkali metal is potassium carbonate.

In this method, the tertiary alcohol is typically t-butanol; however, other tertiary alcohols can be alternatively employed. Such tertiary alcohols include, for example, 2-methyl-2-butanol, 3-ethylpentanol, and other tertiary alcohols, typically containing 6 carbons or fewer.

In this method, the debromination step (step (2) above) occurs under refluxing conditions, which means that, when the tertiary alcohol is t-butanol, which has a boiling point of 82° C., reflux temperature would be about 80-85° C.

In this method, in the step of purifying the dianhydrohexitol from the ether slurry (step (3) above), the ether is typically an aliphatic ether with lower alkyl groups, such as dimethyl ether, methyl ethyl ether, diethyl ether, dipropyl ether, methyl propyl ether, and ethyl propyl ether. However, a preferable ether is diethyl ether.

ADVANTAGES OF THE INVENTION

The present invention provides an improved and efficient method for the synthesis of substituted hexitols, especially dianhydrogalactitol (DAG). The method of the present invention is readily scalable so that large quantities of dianhydrogalactitol can be prepared for pharmaceutical or other use. The method of the present invention produces dianhydrogalactitol in high yield and free from impurities.

Methods according to the present invention possess industrial applicability for the synthesis of substituted hexitols, especially dianhydrogalactitol (DAG), which have uses in pharmacology and elsewhere.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equiva-

The invention claimed is:

1. A method for synthesizing and purifying dianhydrogalactitol (DAG) comprising the steps of:
   (a) reacting dulcitol with a concentrated solution of hydrobromic acid at a temperature of about 80° C. to produce dibromogalactitol;
   (b) reacting the dibromogalactitol with potassium carbonate in t-butanol to produce dianhydrogalactitol; and
   (c) purifying the dianhydrogalactitol using a slurry of ethyl ether to produce purified dianhydrogalactitol.

2. The method of claim 1 wherein the concentrated solution of hydrobromic acid is about 70% hydrobromic acid and is produced by reacting phosphorus with bromine in hydrobromic acid at elevated temperature.

3. The method of claim 1 wherein the dibromogalactitol is dissolved in t-butanol in a proportion of about 1 g of dibromogalactitol to 10 mL of t-butanol.

4. The method of claim 1 wherein the dibromogalactitol is purified by recrystallization prior to its conversion to dianhydrogalactitol.

5. The method of claim 1 wherein the dulcitol is purified from the plant *Maytenus confertiflora* by the steps of:
   (i) soaking the plant *Maytenus confertiflora* in a soaking solution of from about 50% to about 80% of ethanol for about 24 hours;
   (ii) collecting the soaking solution from step (i);
   (iii) repeating the soaking step of step (i) with a fresh soaking solution of from about 50% to about 80% of ethanol for about 24 hours;
   (iv) collecting the soaking solution from step (iii) and combining it with the soaking solution collected in step (ii);
   (v) removing the solvent from the combined soaking solutions of step (iv) by heating under reduced pressure to produce a concentrated solution;
   (vi) allowing the concentrated solution of step (v) to settle overnight and collecting the clear supernatant;
   (vii) extracting the clear supernatant from step (vi) with chloroform and then removing the chloroform under heat and reduced pressure to produce a residue;
   (viii) dissolving the residue from step (vii) in hot methanol and then cooling to allow crystallization; and
   (ix) collecting the collected crystals of dulcitol, filtering, and drying the crystals under reduced pressure.

6. A method for synthesizing and purifying a dianhydrohexitol comprising the steps of:
   (a) reacting a hexitol bearing two epoxide groups with a concentrated solution of hydrobromic acid at a temperature of about 80° C. to produce a dibromohexitol;
   (b) reacting the dibromohexitol with a carbonate salt of an alkali metal in a tertiary alcohol to produce a dianhydrohexitol; and
   (c) purifying the dianhydrohexitol using a slurry of an ether to produce the purified dianhydrohexitol.

7. The method of claim 6 wherein the dianhydrohexitol is selected from the group consisting of dianhydrogalactitol and a substituted dianhydrogalactitol.

8. The method of claim 7 wherein the dianhydrohexitol is dianhydrogalactitol.

9. The method of claim 6 wherein the concentrated solution of hydrobromic acid is about 70% hydrobromic acid and is produced by reacting phosphorus with bromine in hydrobromic acid at elevated temperature.

10. The method of claim 6 wherein the tertiary alcohol is selected from the group consisting of t-butanol, 2-methyl-2-butanol, and 3-ethylpentanol.

11. The method of claim 10 wherein the tertiary alcohol is t-butanol.

12. The method of claim 6 wherein the dibromohexitol is dissolved in the tertiary alcohol in a proportion of about 1 g of dibromohexitol to 10 mL of tertiary alcohol.

13. The method of claim 12 wherein the tertiary alcohol is selected from the group consisting of t-butanol, 2-methyl-2-butanol, and 3-ethylpentanol.

14. The method of claim 13 wherein the tertiary alcohol is t-butanol.

15. The method of claim 6 wherein the dibromohexitol is purified by recrystallization prior to its conversion to dianhydrohexitol.

16. The method of claim 6 wherein the carbonate salt of the alkali metal is a carbonate salt of an alkali metal selected from the group consisting of sodium carbonate and potassium carbonate.

17. The method of claim 16 wherein the carbonate salt of the alkali metal is potassium carbonate.

18. The method of claim 6 wherein the ether is an aliphatic ether with lower alkyl groups.

19. The method of claim 18 wherein the ether is selected from the group consisting of dimethyl ether, methyl ethyl ether, diethyl ether, dipropyl ether, methyl propyl ether, and ethyl propyl ether.

20. The method of claim 19 wherein the ether is diethyl ether.

* * * * *